United States Patent [19]
Lever et al.

[11] Patent Number: 5,965,088
[45] Date of Patent: Oct. 12, 1999

[54] METHOD FOR PROVIDING RAPID DISINFECTION OF CONTACT LENSES

[76] Inventors: Andrea M. Lever; O. William Lever, Jr., both of 14 Fenimore Dr., Pittsford, N.Y. 14534

[21] Appl. No.: 08/956,514

[22] Filed: Oct. 23, 1997

[51] Int. Cl.$^6$ ........................................................ A61L 2/00
[52] U.S. Cl. ................................ 422/28; 422/1; 424/429; 424/464; 514/839; 514/840
[58] Field of Search .......................... 422/28, 1; 514/839, 514/840; 134/901; 510/112; 424/464, 429

[56] References Cited

U.S. PATENT DOCUMENTS

| | | | |
|---|---|---|---|
| 3,428,567 | 2/1969 | Dickinson et al. | 260/2 |
| 4,354,952 | 10/1982 | Riedhammer et al. | 252/106 |
| 4,361,548 | 11/1982 | Smith et al. | 424/78 |
| 4,758,595 | 7/1988 | Ogunbiyi et al. | 514/635 |
| 5,411,597 | 5/1995 | Tsao et al. | 134/26 |
| 5,411,598 | 5/1995 | Tsao et al. | 134/26 |

FOREIGN PATENT DOCUMENTS

| | | | |
|---|---|---|---|
| 0125092 | 11/1984 | European Pat. Off. | C07C 129/16 |
| 0384666 | 8/1990 | European Pat. Off. | A61L 2/18 |
| 0575290 | 12/1993 | European Pat. Off. | A61L 2/18 |
| 2517208 | 6/1983 | France | A61L 2/18 |
| 1095902 | 12/1967 | United Kingdom | C07C 129/08 |
| 1432345 | 4/1976 | United Kingdom | A61K 31/785 |
| 92/11876 | 7/1992 | WIPO | A61L 2/18 |
| 94/19027 | 9/1994 | WIPO | A61L 2/18 |

*Primary Examiner*—Krisanne Thornton
*Attorney, Agent, or Firm*—Chris P. Konkol

[57] ABSTRACT

The present invention is directed to method of disinfecting a contact lens with an ophthalmically safe disinfecting aqueous solution comprising about 2.0 to about 8.0 ppm of a bis(biguanide) having the following formula:

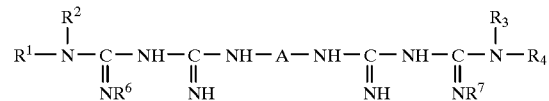

wherein $R^1$ and $R^4$ are independently selected from the group consisting of branched or unbranched alkyl having 4–12 carbon atoms, ether or thioether radical having 4–12 carbon atoms, or cycloalkyl or cycloalkyl-alky radical having 5–12 carbon atoms; $R^2$ and $R^3$ are independently selected from the group consisting of hydrogen, alkyl having 1–12 carbon atoms, alkoxyalkyl having 1–12 carbon atoms, or cycloalkyl or cycloalkyl-alkyl having 5–12, carbon atoms; $R^6$ and $R^7$ are independently selected from the group consisting of hydrogen and alkyl radical having 1–6 carbon atoms, and A in the above formula is selected from the group consisting of a divalent alkyl, alkyloxyalkyl, or alkylsufide radical each having 4–12 carbon atoms. The invention is also directed to a method of cleaning and/or disinfecting a contact lens within a minimum soaking period that is not more than about 75 minutes.

20 Claims, No Drawings

METHOD FOR PROVIDING RAPID DISINFECTION OF CONTACT LENSES

FIELD OF THE INVENTION

This invention relates to new and improved methods for disinfecting contact lenses with ophthalmically safe disinfecting solutions comprising certain bis(biguanides), such that increased microbiocidal efficacy of the solution allows more rapid disinfecting regimens for treating contact lenses.

BACKGROUND OF THE INVENTION

Generally, contact lenses in wide use fall into two categories: (1) hard lenses formed from materials prepared by polymerization of acrylic esters, such as polymethyl methacrylate (PMMA), and the newer rigid gas permeable (RGP) lenses formed from silicone acrylates and fluorosilicone methacrylates and (2) gel, hydrogel or soft type lenses made of polymerized hydrophilic or hydrophobic monomers, such as 2-hydroxyethyl methacrylate (HEMA). The hard acrylic type contact lenses are characterized by low water vapor diffusion constants, resistance to the effects of light, oxygen and hydrolysis and absorb only minor amounts of aqueous fluids. Because of the durability of hard contact lenses, coupled with their tendency not to absorb appreciable amounts of water, the selection of suitable disinfecting agents, cleaning agents or other lens care compounds is relatively non-critical.

However, unlike hard lenses, soft type contact lenses and certain of the newer rigid gas permeable contact lenses have a tendency to bind and concentrate significantly more fluids, environmental pollutants, water impurities, as well as antimicrobial agents and other active ingredients commonly found in lens care solutions. In most instances, the low levels of the ingredients in lens care solutions do not lead to eye tissue irritation when used properly. Nevertheless, because of the inherent binding action of protein deposits to soft lens materials, some disinfecting agents and preservatives tend to build up on lens surfaces and may become concentrated to potentially hazardous levels, such that when released could cause corneal inflammation and other eye tissue irritation.

Previous efforts to alleviate the problem of binding and concentrating disinfectants and preservatives onto contact lens surfaces, and reducing the potential for eye tissue irritation have not been totally satisfactory. For example, in spite of low toxicity levels, not all disinfectants are compatible for use with all types of contact lenses. Although they are effective antibacterial agents, their use can result in a loss of lens hydrophilic properties, cause solution instability or may even lack compatibility with certain types of hard lenses, e.g., high silicon content.

Other antibacterial agents were found to be more compatible with contact lenses and exhibit less binding on lens surfaces. In one case, it was found that chlorhexidine, a biguanide, binds to soft lens material seven times less than benzalkonium chloride, but the presence of proteinaceous oily tear-film deposits can double the amount of chlorhexidine absorbed over that of clean lenses. U.S. Pat. No. 4,354,952 discloses very dilute disinfecting and cleaning solutions containing chlorhexidine or its salts in combination with certain amphoteric and non-ionic surfactants. These solutions were found to reduce the amount of binding of chlorhexidine on hydrophilic soft contact lenses. Notwithstanding the reduction in binding achieved by this invention, the use of chlorhexidine did result in certain tradeoffs. The antimicrobial activity of the chlorhexidine may be diminished when used with certain amphoteric surfactants. Furthermore, it was reported that if not used in proper ratio, the surfactant and disinfectant will precipitate unless a non-ionic type surfactant is also employed.

U.S. Pat. No. 4,361,548 discloses a contact lens disinfectant and preservative containing dilute aqueous solutions of a polymer; namely, polydimethyldiallylammonium chloride (DMDAAC) having molecular weights ranging from about 10,000 to 1,000,000. Amounts of DMDAAC homopolymer as low as 0.00001 percent by weight may be employed when an enhancer, such as thimerosal, sorbic acid or phenylmercuric salt is used therewith. Although lens binding and concomitant eye tissue irritation with DMDAAC were reduced, it was found in some users to be above desirable clinical levels.

British patent 1,432,345 discloses contact lens disinfecting compositions containing a polymeric biguanide and a mixed phosphate buffer. The products embraced by this patent have not found acceptance by the consumer. Corneal staining is an indication of clinical acceptability and compositions as disclosed by this patent have staining values of 17% or more present, far above that which is desirable clinically.

Other efforts to reduce or eliminate soft lens binding have led to the use of anti-binding or detoxifying agents, like polyvinyl pyrrolidone (PVP) and polyvinyl alcohol (PVA). For the most part, however, these polymers alone were found to be ineffective in reducing lens binding and eye tissue irritation.

U.S. Pat. No. 4,758,595 to Ogunbiyi et al. disclosed that a contact-lens solution containing a polyguanide biguanide (PAPB) has enhanced efficacy when combined with a borate buffer. Such solutions are compatible with both hard and soft type lenses, and are adaptable for use with virtually any of the commonly known disinfecting techniques, including "cold" soaking under ambient temperature conditions, as well as with high temperature disinfecting methods. These disinfecting and preservative solutions are especially noteworthy for their broad spectrum of bactericidal and fungicidal activity at low concentrations coupled with very low toxicity when used with soft type contact lenses. Ogunbiyi et al. stated that biguanide polymers in the higher molecular weight ranges usually demonstrate lower toxicity levels than corresponding lower molecular weight materials.

Compositions containing PAPB and borate, or other non-phosphate buffers, have been commercialized in various products, but at levels of about 1.0 ppm or less. It is generally desirable to provide the lowest level of a bactericide possible, while maintaining the desirable level of disinfection efficacy, in order to provide a generous margin for safety and comfort.

Commercially sold contact-lens solutions containing PAPB require a regimen for the use of the product that requires a minimum of four hours soaking time. Obviously, such a soaking requirement is consistent with overnight disinfection and soaking of contact-lens, as is customarily done on a daily basis by contact-lens wearers. However, a contact-lens wearer may have occasion to remove his or her contact lenses for a shorter period of time, for example, while swimming, reading or any other activity where eyeglasses may be preferable for a particular task. Some people may wear eyeglasses for part of the day, for example, during certain work activities and may wear contact lenses for part of the day, for example, during certain social occasions. Removal of lenses at unscheduled times during the day may also occur through the need to remove environmental debris from the lens or may occur thru accidental lens removal, e.g., on occasion by blinking. In such cases, when a contact lens is installed in the eye a plurality of times during a single day, a four-hour soak may be neither practical nor convenient. In the absence of a product that provides more rapid disinfection, reinsertion of lenses that are not properly disinfected may occur. A disinfecting solution that reduces the minimum period of soaking substantially below four hours would, therefore, be desirable.

One would expect that a solution or method requiring a relatively shorter soak time for disinfecting a lens would generally require a more efficacious or stronger disinfectant than a solution or method requiring a relatively longer soak time for disinfection.

U.S. Pat. Nos. 5,411,597 and 5,411,598 to Tsao et al. disclose a contact-lens solution that is designed to disinfect a lens in a relatively short period of time. Such a solution comprises a high concentration of an alkylene glycol and an alkanol. A disadvantage of such a solution is that it is too toxic for contact with the human eye and, accordingly, must be rinsed from the contact lens before inserting the contact lens in the eye.

The stronger the bactericidal effect of a solution, however, the more likely that it may exhibit toxic effects or adversely affect comfort. In fact, many efficacious bactericides used in other contexts, such as mouthwashes, cosmetics, or the like, while being sufficiently safe for use in such products, would be too toxic for ophthalmic use, involving use in the eye. This is particular the case with soft lenses, as indicated above, because of their tendency to bind chemicals.

It would be desirable to obtain a contact-lens solution that could disinfect lenses in less time, whereby the minimum soaking time is reduced, but that would not require rinsing to remove the disinfecting solution. Some of the most popular products for disinfecting lenses are multi-purpose solutions that-can be used to clean, disinfect and wet the lenses, followed by direct "insertion" (placement on the eye) without rinsing. Obviously, the ability to use a single solution for contact lens care is an advantage. Such a solution, however, must be particularly gentle to the eye, since, as indicated above, some of the solution will be on the lens when inserted and will come into contact with the eye.

Accordingly, there is a need for improved solutions or methods for disinfecting contact lenses that can simultaneously provide both (1) a high level of antibacterial activity, such that the minimum soak period can be substantially reduced, and (2) a low order of toxicity to eye tissue, such that the solution can be used to treat contact lenses without rinsing, despite any tendency of disinfectants to bind onto lens surfaces. While challenging to develop, it would be especially desirable to obtain a method of disinfecting lenses with a multi-purpose solution for soft contact lenses, which would allow direct placement of the contact lens on an eye following brief soaking and/or rewetting with the multi-purpose solution.

BRIEF DESCRIPTION OF THE INVENTION

The present invention is directed to method of disinfecting contact lenses with an ophthalmically safe disinfecting solution for contact lenses, which solution comprises about 2.0 to about 8.0 ppm of the hydrochloride salt of a bis (biguanide), or a corresponding concentration of the same bis(biguanide) in the form of the free base or a different water-soluble salt, which bis(biguanide) has the following general formula:

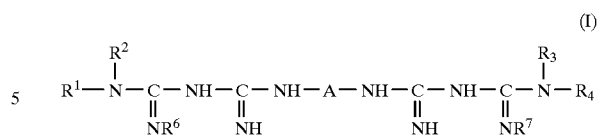

wherein $R^1$ and $R^4$ are independently selected from the group consisting of branched or unbranched alkyl having 4–12 carbon atoms, alkoxyalkyl or alkylsulfide radical having 4–12 carbon atoms, or cycloalkyl or cycloalkyl-alkyl radical having 5–12 carbon atoms; $R^2$ and $R^3$ are independently selected from the group consisting of hydrogen, alkyl having 1–12 carbon atoms, alkoxyalkyl having 1–12 carbon atoms, or cycloalkyl or cycloalkyl-alkyl having 5–12 carbon atoms; $R^6$ and $R^7$ are independently selected from the group consisting of hydrogen and alkyl radical having 1–6 carbon atoms, and A in the above formula is a divalent group having 4–16 carbon atoms and is selected from the group consisting of an alkylene, alkyloxyalkyl, and alkylsufide radical, wherein the aforesaid alkyoxyalkyl or alkylsulfide radicals are either a polymethylene chain interrupted with one or more oxygen and/or sulfur atoms or a polymethylene chain substituted with an alkoxy (—$OR^8$) or alkylthio (—$SR^9$) group, wherein $R^8$ and $R^9$ are independently selected from the group consisting of alkyl having 1–12 carbon atoms or a cycloalkyl or cycloalkyl-alkyl having 5–12 carbons, or wherein A is a divalent polymethylene group having 8 to 16 carbon atoms interrupted with a divalent radical of cyclohexane or 1,4-diaza-cyclohexane.

The solutions used in the present invention may also comprise an effective amount of a buffering agent, preferably in the amount of from about 0.01 to 5% by weight, an effective amount of a surfactant, preferably in an amount of about 0.01% to 5% by weight, and water in an amount of at least about 90% by weight. In one embodiment of the invention, the surfactant is a neutral or non-ionic surfactant.

The invention comprises soaking the lens for a period of not more than 75 minutes in an aqueous solution comprising a microbiocidally effective amount, within the range of from about 2.0 to about 8.0 ppm, preferably 2.0 to 6.0 ppm of a bis(biguanide) of Formula (I) above, in the form of the dihydrochloride salt or a corresponding molar amount of another salt or its free base, in combination with an effective amount of at least one buffering agent, at least one tonicity agent, and at least one surfactant, and then directly placing the treated lens on an eye. In a preferred embodiment of this method, the minimum soaking period ranges from about 10 to about 60 minutes.

DETAILED DESCRIPTION OF THE INVENTION

As indicated above, the present invention is directed to a composition, in the form of an aqueous solution containing a compound of Formula (I) above, and a method of using the solution for disinfecting and/or preserving contact lenses, especially soft contact lenses. The disinfecting solutions of the present invention are effective at low concentrations against a wide spectrum of microorganisms, including but not limited to *Staphylococcus aureus*, *Pseudomonas aeruginosa*, *Serratia marcescens*, *Candida albicans*, and *Fusarium solani*. A disinfecting solution is generally defined as a contact lens care product containing one or more active ingredients (for example, anti-microbial agents and/or preservatives) in sufficient concentrations to destroy harmful microorganisms on the surface of a contact lens within the recommended minimum soaking time. The recommended minimum soaking time is included in the package instructions for use of the disinfecting solution. The present solution, in combination with its container or bottle and packaging, including instructions for use, may be considered a novel and improved kit, package, or system for the care of contact lenses.

By the term "soft lens" is meant a lens having a proportion of hydrophilic repeat units such that the water content of the lens during use is at least 20% by weight. The term "soft contact lens" as used herein generally refers to those contact lenses which readily flex under small amounts of force. Typically, soft contact lenses are formulated from polymers having a certain proportion of repeat units derived from hydroxyethyl methacrylate and/or other hydrophilic monomers, typically crosslinked with a crosslinking agent. In contrast, conventional "hard contact lenses", which cover only a part of the cornea of the eye, usually consist of poly(methyl methacrylate) crosslinked with ethylene glycol dimethacrylate or the like, and conventional rigid gas permeable lenses (RGP) typically consists of monomers containing silicon that result in a more oxygen-permeable material.

By the term "ophthalmically safe" with respect to a contact-lens solution is meant that a contact lens treated with the solution is safe for direct placement on the eye without rinsing, that is, the solution is safe and sufficiently comfortable for daily contact with the eye via a contact lens. An ophthalmically safe solution has a tonicity and pH that is compatible with the eye and comprises materials, and amounts thereof, that are non-cytotoxic according to international ISO standards and U.S. FDA regulations.

By the term "disinfecting solution" is meant a solution containing one or more microbiocidal compounds, that is effective for reducing or substantially eliminating the presence of an array of microorganisms present on a contact lens, which can be tested by challenging a solution or a contact lens after immersion in the solution with specified inoculums of such microorganisms. The term "disinfecting solution" as used herein does not exclude the possibility that the solution may also be useful for a preserving solution or that the disinfecting solution may additionally be useful for daily cleaning, rinsing and storage of contact lenses.

A solution that is useful for cleaning, chemical disinfection, storing, and rinsing a contact lens is referred to herein as a "multi-purpose solution." Such solutions may be part of a "multi-purpose solution system" or "multi-purpose solution package." The procedure for using a multi-purpose solution, system or package is referred to as a "multi-functional disinfection regimen." Multi-purpose solutions do not exclude the possibility that some wearers, for example, wearers particularly sensitive to chemical disinfectants or other chemical agents, may prefer to rinse or wet a contact lens with a another solution, for example, a sterile saline solution prior to insertion of the lens. The term "multi-purpose solution" also does not exclude the possibility of periodic cleaners not used on a daily basis or supplemental cleaners for removing proteins, for example enzyme cleaners, which are typically used on a weekly basis. By the term "cleaning" is meant that the solution contains one or more active ingredients in sufficient concentrations to loosen and remove loosely held lens deposits and other contaminants on the surface of a contact lens, especially if used in conjunction with digital manipulation (for example, manual rubbing of the lens with a solution) or with an accessory device that agitates the solution in contact with the lens, for example, a mechanical cleaning aid.

According to the present invention, the bis(biguanide) germicides employed in the present solutions include compounds, and their water-soluble salts, having following formula:

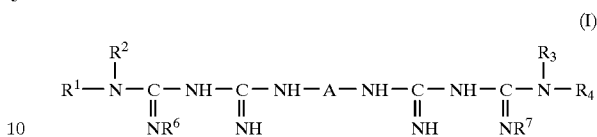

wherein $R^1$ and $R^4$ are independently selected (i.e., the same or different) from the group consisting of branched or unbranched alkyl having 4–12, preferably 6–10, carbon atoms, alkoxyalkyl (i.e., ether) or alkylsulfide (thioether or dialkylsufide) radical having 4–12, preferably 6–10, carbon atoms, or cycloalkyl or cycloalkyl-alkyl radical having 5–12, preferably 7–10, carbon atoms; $R^2$ and $R^3$ are independently selected from the group consisting of hydrogen, alkyl having 1–12, preferably 1–6, carbon atoms, alkoxyalkyl having 1–12, preferably 1–6, carbon atoms, or cycloalkyl or cycloalkyl-alkyl having 5–12, preferably 6–10, carbon atoms; $R^6$ and $R^7$ are independently selected from the group consisting of hydrogen and alkyl radical having 1–6 carbon atoms, and A in the above formula is a divalent group having 4–16 carbon atoms, preferably 6–10, carbon atoms and is selected from the group consisting of an alkylene (a divalent radical of an aliphatic hydrocarbon), alkyloxyalkyl, and alkylsufide radical, wherein the aforesaid alkyoxyalkyl or alkylsulfide radicals are either a polymethylene chain interrupted with one or more oxygen and/or sulfur atoms or a polymethylene chain substituted with an alkoxy (—$OR^8$) or alkylthio (—$SR^9$) group, wherein $R^8$ and $R^9$ are independently selected from the group consisting of alkyl having 1–12 carbon atoms, or a cycloalkyl or cycloalkyl-alkyl having 5–12 carbon, or wherein A is a divalent polymethylene group having 8 to 16 carbon atoms, preferably 6 to 12 carbon atoms interrupted with a divalent radical of a cyclohexane or diaza-cyclohexane ring (a 1,4-diazacyclohexane or piperazine connected to the polymethylene ring via the nitrogen atoms). By the term "cycloalkyl," either in cycloalkyl or cycloalkyl-alkyl, is meant unsubstituted or substituted cycloalkyl, where the substituents are one or more alkyl, alkoxy (—OR), or alkylsulfide (—SR) groups having 1–6 carbon atoms.

In the disinfecting solution used in the present method, the biguanides of Formula (I) are suitably used in the total amount (with respect to the weight of the hydrochloride salt, often containing two hydrochlorides as in alexidine) of 2.5 to 8.0 ppm, preferably 2.5 to 6.0 ppm based on the total aqueous solution, or corresponding molar amounts when in the form of another salt or its free base. More preferably, the bis(biguanides) are used in the molar amount corresponding to 3.0 to 5.0 ppm, most preferably 3.5 to 4.5 ppm. of the hydrochloride salt. When the bis(biguanide) that is used in the present invention is in the form of the free base or a salt other than the hydrochloride, then the above-indicated ppm ranges must be adjusted to obtain the corresponding ppm ranges such that the ranges are the same on a molar basis as for the dihydrochloride salt of the bis(biguanide). The concentration of the bis(biguanide) in solution is generally directly related to its bactericidal efficacy. The corresponding weight of an equal molar amount or concentration of a different salt form of a bis(biguanide) or its free base can be readily calculated, for use in weighing out a suitable amount of the substance on hand whatever its form. The term "ppm" refers to "parts per million" and 1.0 ppm corresponds to 0.00010 weight percent. It is based on the total weight of the composition or, in this case, the total weight of the aqueous disinfecting solution.

In the present application, the amount of the bis (biguanide) or other components in a solution used in the present method refers to the amount formulated and introduced into the solution at the time the solution is made. Over time (for example, over a storage period of 18 months), the assayed amount of a bis(biguanide) in solution may decrease. For various reasons, however, the assayed amount may not be a good indicator of the remaining efficacy of the solution and any such decrease over time is taken into account when initially formulating a product.

Preferably, the bis(biguanide) compounds have the following formula:

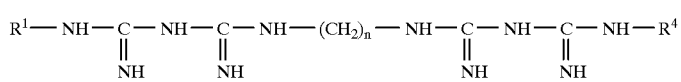
(II)

or their water-soluble salt form, wherein $R^1$ and $R^4$ are independently selected from the group consisting of branched or unbranched alkyl, alkoxyalkyl (i.e., ether) or alkylsulfide (thioether) radical, and n is 5 to 7.

Each of $R^1$ and $R^4$ in Formulas (I) or (II) above may be, for example, an n-butyl, isobutyl, sec-butyl, tert-butyl, pentyl, neopentyl, octyl, 2-ethylhexyl, dodecyl, cyclobutyl, cyclopentyl, cyclohexyl, cycloheptyl, cyclopentylmethyl or cyclohexylmethyl radical. Preferred are 2-ethylhexyl (alexidine), 1,5-dimethylhexyl, 1-methylhexyl, 1,3-dimethylpentyl, 1,4-dimethylpentyl, cyclohexylmethyl, 2-norbornyl, propyloxyoctyl, and propyloxybutyl.

Each of $R^2$ and $R^3$ in Formula (I) above may be, for example, a methyl, ethyl, n-propyl, isopropyl, n-butyl, isobutyl, sec-butyl, tert-butyl, pentyl, neopentyl, octyl, 2-ethylhexyl, dodecyl, cyclobutyl, cyclopentyl, cyclohexyl, cycloheptyl, cyclopentylmethyl or cyclohexylmethyl radical. When one or more of $R^2$ and $R^3$ is an alkoxyalkyl radical, it may be, for example, a 2-methoxyethyl.

Each of $R^6$ and $R^7$ in Formula I may be, for example, a methyl, ethyl, n-propyl, isopropyl, n-butyl, isobutyl, sec-butyl, tert-butyl, pentyl, or neopentyl radical.

Preferred A groups in Formula (I) include hexamethylene and a divalent hexamethylene interrupted with a divalent radical derived from 1,4-diaza-cyclohexane in which the nitrogen atoms are connected to alkylene groups having 1 to 4 carbon atoms, for example, resulting from the starting material N,N'-(2-aminoethyl)-1,4 piperadine or the like.

The acid-addition salts of the invention may be derived from an inorganic or organic acid. In most circumstances it is preferable that the salts be derived from an acid which affords an anion which is suitable for human usage, for example a pharmaceutically-acceptable anion. Examples of such acids are hydrochloric, hydrobromic, phosphoric, sulphuric, acetic, D-gluconic, 2-pyrrolidino-5-carboxylic, methanesulphonic, carbonic, lactic and glutamic acids.

The bis(biguanides) of Formula (I) preferably have relatively hydrophobic end groups. Preferably, the Log P of the compounds is 5 to 10, preferably 6 to 8, wherein P is the partition coefficient of the free base, using the following equation, wherein α is the degree of ionization:

$$P = \frac{C_{octanol}}{C_{buffer}(1-\alpha)}$$

To obtain the partition coefficient of a bis(biguanide), the compound is partitioned between a 0.05 M phosphate buffer (pH 11) saturated with octanol and octanol saturated with phosphate buffer after gentle shaking at room temperature (26° C.). The volume ratio of these two phases and the amount of sample are chosen so that the absorbance of the sample from the buffered layer after partitioning has a value between 0.2 and 0.9, using a 1-cm cell and buffer solution as a blank. By working at a fixed pH and knowing or calculating the $pK_a$, the P value can be determined using the above formula. See "Quantitative Structure-Activity Relationships for Biguanides, Carbamidates, and Bisbiguanides as Inhibitors of Streptococcus mutans NO. 6715", Warner, V. and Lynch, D., *J. Med. Chem*, 1979, Vol. 22, no. 4 at 359, 365; and Albert, and Serjeant, E., "Determination of Ionization and Stability Constants," Butler and Tanner Ltd., London, England, 1962, both references hereby incorporated by reference.

Examples of preferred bis(biguanide) compounds of this invention are 2-(decylthiomethyl)-pentane-1,5-bis(5-isopropylbiguanide), 2-(decylthio-methyi)pentane-1,5-bis (5,5-diethylbiguanide), and hexane-1,6-bis(2-ethylhexylbiguanide), the latter also known as alexidine or 1,1'-hexamethylenebis(5-(2-ethylhexyl)-biguanide) dihydrochloride. Other preferred bis(biguanides) include 1,1'-hexamethylenebis(5-heptyl-biguanide) dihydrochloride, 1,1'-hexamethylenebis(5-octyl-biguanide) dihydrochloride, and 1,1'-hexamethylenebis(5-hexyl-biguanide) dihydrochloride.

The biguanide compounds of Formula (I) wherein $R^6$ and $R^7$ are each hydrogen may be made by reacting a bis-cyanoguanidine of the formula:

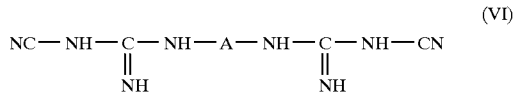
(VI)

with an amine $R^1R^2NH$, or with two different amines $R^1R^2NH$ and $R^3R^4NH$, in the form of an acid addition salt thereof, wherein A, $R^1$, $R^2$, $R^3$ and $R^4$ have the meanings stated above, at a temperature of 100° C. to 170° C. A preferred amine salt is the hydrochloride. Most diamines are commercially available from a variety of sources.

The reactants are heated together until the reaction is complete. The reaction proceeds fastest at higher temperatures, but if thermal stability is a problem, the reaction should be carried out at lower temperature for a longer period. The reactants are most conveniently melted together in the absence of a solvent, but if desired an inert solvent such as DMSO 2-methoxyethanol, 2-ethoxyethanol, nitrobenzene, sulpholane, isopropanol, n-butanol, ethylene glycol dimethyl ether or water, or a mixture of such solvents, may be used.

The bis-cyanoguanidine of Formula (VI) may be manufactured from known starting materials such as hexamethylenedinitrile which is reduced, for example, with hydrogen and Raney nickel or with borane in dimethyl sulphide to the corresponding diamine of Formula (VIII), and the diamine in the form of an acid-addition salt, conveniently the dihydrochloride, is reacted with sodium dicyanamide or other suitable salt to form the required starting material of Formula (VI), as depicted below.

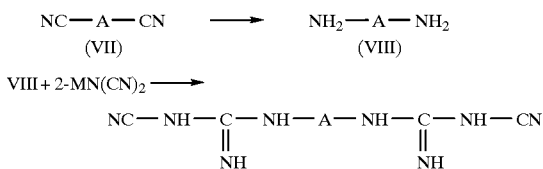

wherein M is a sodium, potassium, zinc or other suitable salt. The sodium salt is commercially available.

The compounds of the present invention can also be made by reacting a diamine of Formula (VIII) in the form of an acid addition salt, with a cyanoguanidine of the formula:

or with a cyanoguanidine of Formula (IX) and a cyanoguanidine of the formula:

$$R^3R^4N-\underset{\underset{NR^7}{\|}}{C}-NH-CN \quad (X)$$

and wherein A, $R^1$, $R^2$, $R^3$, $R^4$, $R^6$ and $R^7$ have the meanings stated above, at a temperature of 100° to 170° C.

A suitable salt of the diamine is, for example, the dihydrochloride. The reactants are heated together until the reaction is complete. The reaction proceeds fastest at higher temperature, but if thermal stability is a problem, the reaction should be carried out at lower temperature over a longer period. If a melt can be formed at those temperatures the reactants are conveniently melted together in the absence of a solvent. If not, or alternatively, the reactants are heated together in a suitable inert solvent, for example those mentioned above. The acid-addition salts of the invention are obtained by conventional means.

The cyanoguanidines of the Formulae (IX) and (X) wherein $R^6$ and $R^7$ are hydrogen, which may be used as starting materials in the above process, may be obtained by reacting sodium dicyanamide with an appropriate amine $R^1R^2NH$ or $R^3R^4NH$, in the form of an acid-addition salt, conveniently the dihydrochloride, in a suitable inert solvent.

The cyanoguanidines of Formulae (IX) and (X) wherein $R^6$ and $R^7$ are other than hydrogen, which may be used as starting materials in the above process, may be obtained by reacting a dialkyl (cyanoimido)dithio-carbonate, for example dimethyl (cyanoimido)dithio-carbonate, with appropriate amines $R^1R^2NH$ and $R^6NH_2$ or $R^3R^4NH$ and $R^7NH_2$.

For example, alexidine is produced from the following sequence of reactions.

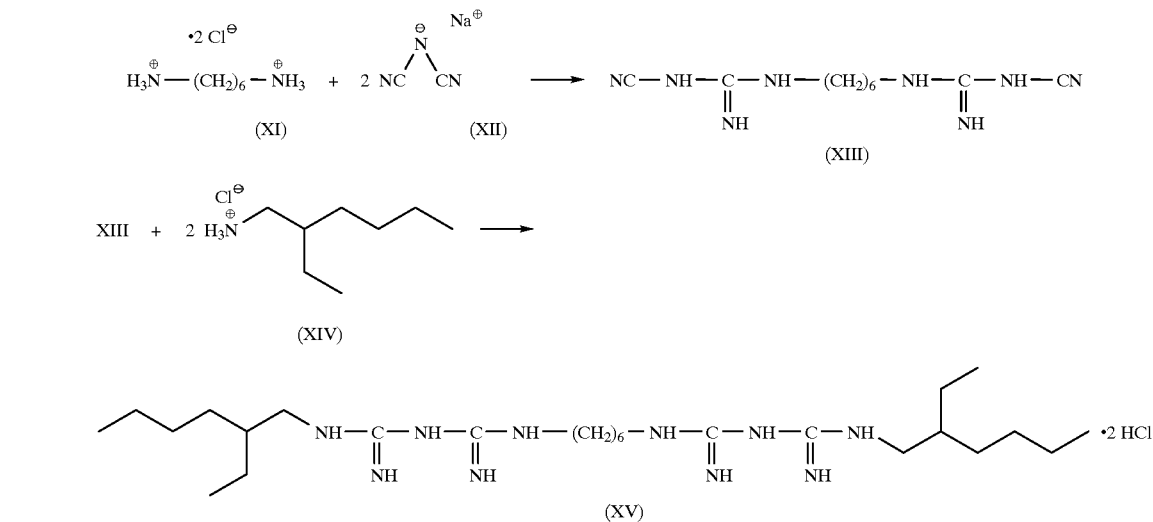

Compound (XI) is hexamethylenediamine dihydrochloride (MW 189), Compound (XII) is sodium dicyanamide, Compound XIII is HMBDA, hexamethylene bis(cyanoguanido), Compound (XIV) is 2-ethyl-hexylamine hydrochloride (MW 165.7), Compound (XV) is alexidine dihydrochloride a.k.a. [1,6-bis-(2-ethylhexylbiguanido]hexane dihydrochloride a.k.a. hexane-1,6-bis(2-ethylhexyl biguanide) dihydrochloride. This compound has a MW (molecular weight I g/mole) of 581.7 and empirical formula $C_{26}H_{56}N_{10} \cdot 2HCl$. The Compound (XV) is commercially available from various sources, including Sigma Chemical Co. (St Louis, Mo.).

Various compounds can be made by appropriate starting materials, for example, where "A" in Formula (I) above is a alkoxy or thioalkyl substituted alkylene, a compound according to Formula (VII) may be made from hexenedinitrile by reaction with $R^5YH$, where Y is an oxygen or sulfur atom as a strong base. Various compounds of Formula (I), where $R^2$ and $R^3$ are H, can be readily obtained as N derivatives of 1,6-bis biguanidohexane.

The methods for synthesized compounds of the present invention are also disclosed in European Patent Application Publication No. 0 125 092 (published Nov. 14, 1984); Rose, F. L. and Swain, G., "Bisdiguanide Having Antibacterial Activity," *J. Chem. Soc.*, p. 4422–4425 (1956); Warner, Victor D. and Lynch, Donald, "Quantitative Structure-Activity Relationships of Biguanide, Carbamimidates, and Bisdiguanides as Inhibitors of Streptococcus Mutans No. 6715, " *J. Med. Chem.*, Vol. 22, No. 6, p. 359–366 (1979).

A second disinfectant/germicide can be employed as a solution preservative, but it may also function to potentiate, compliment or broaden the spectrum of microbiocidal activity of Formula (I). This includes microbiocidally effective amounts of germicides which are compatible with and do not precipitate in the solution, in concentrations ranging from about 0.00001 to about 0.5 weight percent, and more preferably, from about 0.0001 to about 0.1 weight percent. Suitable complementary germicidal agents include, but are not limited to thimerosol, sorbic acid, alkyl triethanolamines, phenylmercuric salts, e.g. nitrate, borate, acetate, chloride and mixtures thereof Suitable salts are soluble in water at ambient temperature to the extent of at least 0.5 weight percent. These salts include the gluconate, isethionate, (2-hydroxyethanesulfonate), formate, acetate, glutamate, succinanate, monodiglycollate, methanesulfonate, lactate, isobutyrate and glucoheptonate.

Further embodiments of potentiating or complementary disinfecting agents for use in the present invention also include certain quaternary ammonium compounds which possess a generally wide spectrum of bactericidal activity and wetting properties. Representative examples of the quaternary ammonium compounds are compositions comprised of balanced mixtures of n-alkyl dimethyl benzyl ammonium chlorides. Other examples include polymeric quaternary ammonium salts used in ophthalmic applications such as polyquaternium 1® (chemical registry number 75345-27-6) available from Onyx corporation.

In another embodiment of the present invention, the bis(biguanides) defined above may be used in combination with lesser amounts of other bis(biguanides), for example chlorhexidine. Such compounds have been disclosed in greater detail in United Kingdom patent specification No. 705,838.

Finally, the bis(biguanides) of the present invention (Formula I or II) may be used in combination with polymeric biguanides, and water-soluble salts thereof, having the following formula:

$$X^1\text{---}[Z\text{---}NH\text{---}\underset{\underset{NH}{\|}}{C}\text{---}NH\text{---}\underset{\underset{NH}{\|}}{C}\text{---}NH]_n\text{---}Z\text{---}X^2 \quad (IV)$$

wherein Z is an organic divalent bridging group which may be the same or different throughout the polymer, n is at least 3, preferably and $X^1$ and $X^2$ are independently selected from the groups —$NH_2$ and

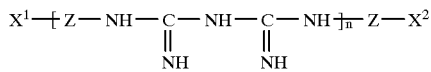

In the above formula, n is preferably 5 to 20. One preferred group of water-soluble polymeric biguanides will have average molecular weights of at least 1,000 and more preferably will have average molecular weights from 1,000 to 50,000. Suitable water-soluble salts of the free bases include, but are not limited to hydrochloride, borate, acetate, gluconate, sulfonate, tartrate and citrate salts.

The above-disclosed biguanides and methods of preparation are described in the literature. For example, U.S. Pat. No. 3,428,576 describes the preparation of polymeric biguanides from a diamine and salts thereof and a diamine salt of dicyanimide.

The polymeric biguanides, in combination with the bisbiguanides of the present invention, are effective in concentrations as low as 0.00001 weight percent (0.1 ppm). It has also been found that the bactericidal activity of the solutions may be enhanced or spectrum of activity broadened through the use of such polymeric biguanides. As a result, the total concentration of disinfectant of Formula (I) when used in combination with a polymeric biguanide of Formula (V) may be lowered further due to complimentary bactericidal activity, which is most desirable in achieving the lowest possible potential for lens binding, concentrating and eye tissue inflammation. Thus, the effective concentration of the polymeric biguanides may be as low as about 0.000010 weight percent (0.10 ppm) and up to about 0.00030 weight percent (3.0 ppm) in the present invention, irrespective of the salt form or whether a free base.

Most preferred are the polymeric hexamethylene biguanides (commercially available as the hydrochloride salt from Zeneca, Wilmington, DE under the trademark Cosmocil™ CQ), their polymers and water-soluble salts being most preferred, referred to as polyaminopropyl biguanide (also sometimes referred to as PAPB or PHMB). The term polyhexamtheylene biguanide, as used herein, is meant to encompass one or more biguanides having the following formula:

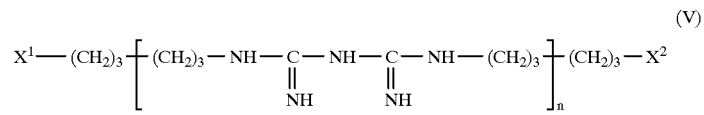

wherein $X^1$ and $X^2$ are as defined above and n is from 1 to 500.

Depending on the manner in which the biguanides are prepared, the predominant compound falling within the above formula may have different $X^1$ and $X^2$ groups or the same groups, with lesser amounts of other compounds within the formula. Such compounds are known and are disclosed in U.S. Pat. No. 4,758,595 and British Patent 1,432,345, which patents are hereby incorporated herein by reference. Preferably, the water-soluble salts are compounds where n has a value of 2 to 12, most preferably 3 to 8.

The solutions used in the present invention may comprise at least one surfactant. Suitable surfactants can be either amphoteric, cationic, anionic, or nonionic which may be present (individually or in combination) in amounts up to 15 percent, preferably up to 5.0 percent by weight of the composition or solution. Preferred surfactants are amphoteric or nonionic surfactants, which when used impart cleaning and conditioning properties. The surfactant should be soluble in the lens care solution and non-irritating to eye tissues. Many nonionic surfactants comprise one or more chains or polymeric components having oxyalkylene (—O—R—) repeats units wherein R has 2 to 6 carbon atoms. Preferred non-ionic surfactants comprise block polymers of two or more different kinds of oxyalkylene repeat units, which ratio of different repeat units determined the HLB of the surfactant. Satisfactory non-ionic surfactants include polyethylene glycol esters of fatty acids, e.g. coconut, polysorbate, polyoxyethylene or polyoxypropylene ethers of higher alkanes ($C_{12}$–$C_{18}$). Examples of the preferred class include polysorbate 20 (available under the trademark Tween 20), polyoxyethylene (23) lauryl ether (Brij® 35), polyoxyethyene (40) stearate (Myrj® 52), polyoxyethylene (25) propylene glycol stearate (Atlas® G 2612). One non-ionic surfactant in particular consisting of a poly(oxypropylene)-poly(oxyethylene) adduct of ethylene diamine having a molecular weight from about 7,500 to about 27,000 wherein at least 40 weight percent of said adduct is poly(oxyethylene) has been found to be particularly advantageous for use in cleaning and conditioning both soft and hard contact lenses when used in amounts from about 0.01 to about 15 weight percent. The CTFA Cosmetic Ingredient Dictionary's adopted name for this group of surfactants is poloxamine. Such surfactants are available from BASF Wyandotte Corp., Wyandotte, Michigan, under the registered trademark "Tetronic". An analogous of series of surfactants, also suitable for use in the present invention, is the poloxamer series which is a poly(oxyethylene) poly (oxypropylene) block polymers available under the trademark "Pluronic" (commercially available form BASF).

Various other ionic as well as amphoteric and anionic surfactants suitable for in the invention can be readily ascertained, in view of the foregoing description, from *McCutcheon's Detergents and Emulsifiers*, North American Edition, McCutcheon Division, MC Publishing Co., Glen Rock, N.J. 07452 and the *CTFA International Cosmetic Ingredient Handbook*, Published by The Cosmetic, Toiletry, and Fragrance Association, Washington, D.C. Various non-surfactants may be added to enhance cleaning, for example, certain phosphonates such as Dequest® 2010 phosphonate.

Amphoteric surfactants suitable for use in the present invention include materials of the type are offered commercially under the trade name "Miranol". Another useful class of amphoteric surfactants may be exemplified by the following chemical structure are exemplified by cocoamidopropyl betaine commercially available under the tradename Amphoso® CA.

The foregoing surfactants when employed with a buffer enhancer will generally be present in an amount from 0.01 to 5.0 percent (w/w), preferably 1.0 to 5.0 percent Generally, the solutions used in the present invention for treating contact lenses are also adjusted with tonicity agents, preferably to approximate the osmotic pressure of normal lacrimal fluids which is equivalent to a 0.9 percent solution of sodium chloride or 2.5 percent of glycerol solution. The solutions can be made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation.

The pH of solutions used in the present invention should be maintained within the range of 5.0 to 8.0, more preferably about 6.0 to 8.0, most preferably about 6.5 to 7.8, suitable buffers may be added, such as boric acid, sodium borate, potassium citrate, citric acid, sodium bicarbonate, TRIS, and various mixed phosphate buffers (including combinations of $Na_2HPO_4$, $NaH_2PO_4$ and $KH_2PO_4$) and mixtures thereof Borate buffers are preferred, particularly for enhancing the efficacy of biguanides. Suitably, buffers are used in amounts ranging from about 0.05 to 2.5 percent by weight, and preferably, from 0.1 to 1.5 percent. The disinfecting/preserving solutions of this invention preferably contain a borate or mixed phosphate buffer, containing one or more of boric acid, sodium borate, potassium tetraborate, potassium metaborate or mixtures of the same.

In addition to buffering agents, in some instances it may be desirable to include sequestering agents in the present solutions in order to bind metal ions which might otherwise react with the lens and/or protein deposits and collect on the lens. Ethylene-diaminetetraacetic acid (EDTA) and its salts (disodium) are preferred examples. They are usually added in amounts ranging from about 0.01 to about 0.2 weight percent. Other suitable sequestering agents include gluconic acid, citric acid, tartaric acid and their salts, e.g. sodium salts.

Aqueous solutions of the bis(biguanides) of Formula (I) are especially useful for soft contact lenses, with or without further additives. Nevertheless, the solutions of the present invention may be formulated into specific contact-lens care products, such as wetting solutions, soaking solutions, cleaning and conditioning solutions, as well as multipurpose type lens care solutions. Various additives may make the solutions more acceptable to the user in terms of greater comfort. However, the additives must be non-toxic and compatible with contact lenses.

It may also be desirable to include water-soluble viscosity builders in the solutions of the present invention. Because of their demulcent effect, viscosity builders have a tendency to enhance the lens wearer's comfort by means of a film on the lens surface cushioning impact against the eye. Included among the water-soluble viscosity builders are the cellulose polymers like hydroxyethyl or hydroxypropyl cellulose, carboxymethyl cellulose and the like. Such viscosity builders may be employed in amounts ranging from about 0.01 to about 4.0 weight percent or less. The present solutions may also include optional demulcents.

The aqueous solutions according to the present invention can be effectively used in disinfecting contact lenses by any of the well recognized methods. The lenses may be treated at about room temperature. The lenses are then removed from the solution and may be rinsed with the same or a different solution, for example a preserved isotonic saline solution and then replaced on the eye.

In a first embodiment of a method according to the present invention, the lens is rubbed with a multi-purpose solution according to the present invention, followed by soaking for a total period of time that is within a range of 5 minutes to 75 minutes, prior to direct placement, corresponding to a minimum required (or recommended) soaking period that is a given time period in the same range. By the term "direct placement" is herein meant that the solution is not diluted or rinsed off the lens with a different contact-lens solution prior to "insertion" or placement on the eye.

In a preferred regimen, the soaking time may be about 7.5 to about 60 minutes, more preferably may be about 10 minutes to about 45 minutes, most preferably may be about 10 minutes to about 30 minutes, with corresponding minimum recommended (or required) soaking periods not more than about 60 minutes, preferably not more than about 45 minutes, more preferably not more than about 30 minutes.

Specifically, a solution having a minimum soaking period of 10 minutes, requiring a soaking period of at least 10 minutes, is especially preferred for use by contact-lens wearers.

The following Examples illustrate the compositions and methods of the instant invention.

EXAMPLE 1

This Example illustrates the preparation of 1,6-bis (cyanqguanidino)hexane, used, as a starting material for bis(biguanides) of the present invention. In the amount of 35.80 g (0.402 mole), sodium dicyanamide ($NaC_2N_3$) is suspended in 400 mL of 1-butanol. Then, 23.60 g (0.204 mole) of 1,6-hexanediamine were added as well as 33.0 mL of conc. aqueous hydrochloric acid (0.400 mole). A milky white precipitate appeared immediately which was probably the amine hydrochloride. The mixture was then refluxed for 3.5 hr. The suspension was then cooled to room temperature and filtered. The white solid was then washed well with distilled water before drying under vacuum. Yield 46.38 g; 93.1%. C 10 H 18 N 8 calc'd: C 48.0%; H 7.20%; N 44.80%; found: C 47.7%; H 7.40%; N 45.12%. 300 MHz $^1$H NMR ($d^6$-DMSO) 6.60 ppm (6p, br m); 2.93 ppm (4p, m); 1.34 ppm (4p, br s); 1.15 ppm (4p, br s). IR (KBr pellet, $cm^{-1}$) 3142 (m); 2943; 2912; 2862 (w); 2179 (s); 1658; 1609 (s).

EXAMPLE 2

This Example illustrates the preparation of alexidine for use in the present invention. The compound 1,6-Bis (cyanoguanidino)hexan in the amount of 1.003 g (0.004498 moles) was placed into a flask. To this was added 1.474 mL (1.163 g; 0.008996 moles) of 2-ethylhexylamine. Then, 0.74 mL (0.008996 moles) of concentrated HCl was added. The mixture was heated in a flask to boil away the $H_2O$. After the $H_2O$ was gone, the temperature of the melt had risen to 195° C. The temperature was decreased to 150–160° C. and maintained for 1 hour. The material was cooled to room temperature. The solid can be dissolved in hot water and allowed to crystallize.

EXAMPLE 3

This Example illustrates the preparation of poly (hexamethylene biguanide), also referred to as PAPB or PHMB, for use in combination with bis(biguanides) in the present invention. In 500 mL of distilled water was suspended 25.08 g (0.100 mole) of 1,6-bis(cyanoguanidino) hexane and 18.99 g (0.100 mole) of 1,6-hexanediamine dihydrochloride. The pH of this mixture was then brought down to 6.8 with dilute hydrochloric acid. The water was then removed by distillation under reduced pressure. The white solid was then transferred to a three-necked flask fitted with a mechanical stirrer and heating mantle. The intimate mixture of solids was then placed under nitrogen and the temperature of the mixture was raised to 150–55° C. The molten reaction mixture possessed the consistency of honey. The mixture was stirred at 150–55° C. for 1–1.5 hr. before cooling to room temperature. The resulting poly (hexamethylene biguanide) is obtained as a glassy solid. The yield is essentially quantitative. Melting range 105–125° C. 300 MHz $^1$H NMR ($D_2O$) 3.13 ppm (21.1p, br t); 2.93 ppm (2p, t); 1.49 ppm (21.1p, br s); 1.28 ppm (21.1 p, br s). IR (KBr pellet, $cm^{-1}$) 3325; 3201 (s); 2931; 2858 (m); 2175 (m-w); 1631; 1589; 1550(s).

EXAMPLE 4

This Example illustrates the preparation of an aqueous contact-lens disinfectant solution for use in the present invention.

TABLE 1

| | Percent (w/v) |
|---|---|
| Alexidine.2HCl | 0.0004 |
| Poloxamine 1107** | 1.0 |
| $Na_2$EDTA | 0.11 |
| Boric Acid | 0.66 |
| Sodium Borate | 0.10 |
| Sodium Chloride | 0.54 |
| Distilled Water qs | 100.0 |

**molecular weight 14,500, 70% (w/v) Tetronic ® 1107, a poly (oxypropylene) poly(oxyethylene) block copolymer adduct of ethylene diamine, a trademark of BASF Wyandotte Corp., Wyandotte, MI.

The solution is prepared by gradually heating 80 percent of the water to 80° C. while dissolving the disodium EDTA therein. The boric acid and sodium borate are added to the heated solution of disodium EDTA and dissolved. The sodium chloride is then added to the solution and dissolved, followed by the addition of surfactants. The solution is sterilized by autoclaving to 120° C. for 45 minute. After the solution is cooled to room temperature, the bis(biguanide) is added through a sterile filter, followed by the balance of distilled water. The solution is packaged in sterilized plastic containers.

EXAMPLE 5

This Example illustrates the microbiocidal efficacy of solutions according to the present invention. The antimicrobial efficacy of each of various compositions for the chemical disinfection of contact lenses was evaluated. Microbial challenge inoculums were prepared using *Pseudomonas aeruginosa* (ATCC 9027), *Staphylococcus aureus* (ATCC 6538), *Serratia marcescens* (ATCC 13880), *Candida albicans* (ATCC 10231), and *Fusarium solani* (ATCC 36031). The test organisms were cultured on appropriate agar and the cultures were harvested using sterile DPBST (Dulbecco's Phosphate Buffered Saline plus 0.05% w/v polysorbate 80) or a suitable diluent and transferred to a suitable vessel. Spore suspensions were filtered through sterile glass wool to remove hyphal fragments. *Serratia marcescens*, as appropriate, was filtered (eg., through a 1.2 $\mu$ filter) to clarify the suspension. After harvesting, the suspension was centrifuged at no more than 5000× g for a maximum of 30 minutes at 20–25° C. The supernatant was poured off and resuspended in DPBST or other suitable diluent. The suspension was centrifuged a second time, and resuspended in DPBST or other suitable diluent. All challenge bacterial and fungal cell suspensions were adjusted with DPBST or other suitable diluent to $1\times10^7$–$10^8$ cfu/mL. The appropriate cell concentration may be estimated by measuring the turbidity of the suspension, for example using a spectrophotometer at a preselected wavelength, for example 490 nm. One tube was prepared containing a minimum of 10 mL of test solution per challenge organism. Each tube of the solution to be tested was inoculated with a suspension of the test organism sufficient to provide a final count of $1.0\times10^5$–$10^6$ cfu/mL, the volume of the inoculum not exceeding 1% of the sample volume. Dispersion of the inoculum was ensured by vortexing the sample for at least 15 seconds. The inoculated product was stored at 10–25° C. Aliquots in the amount of 1.0 mL were taken of the inoculated product for determination of viable counts after certain time periods of disinfection. The time points for the bacteria were 25, 50, 75, and 100% of the minimum disinfection time. Yeast and mold were tested at an additional timepoint of at least 400% of the minimum disinfection time. The suspension was mixed well by vortexing vigorously for at least 5 second. The 1.0 mL aliquots removed at the specified time intervals were subjected to a suitable series of decimal dilutions in validated neutralizing media. The suspensions were mixed vigorously and incubated for a suitable period of time to allow for neutralization of the microbial agent. The viable count of organisms was determined in appropriate dilutions by preparation of triplicate plates of trypticase soy (TSA) agar for bacteria and Sabouraud dextrose agar (SDA) for mold and yeast. The bacterial recovery plates were incubated at 30–35° C. for 2–4 days. The yeast was incubated at 20–30° C. for 2–4 days and mold recovery plates at 20–25° C. for 3–7 days. The average number of colony forming units was determined on countable plates. Countable plates refer to 30–300 cfu/plates for bacteria and yeast, and 8 to 80 cfu/plate for mold except when colonies are observed only for the $10^0$ or $10^{-1}$ dilution plates. The microbial reduction was then calculated at the specified time points. In order to demonstrate the suitability of the medium used for growth of the test organisms and to provide an estimation of the initial inoculum concentration, inoculum controls were made by dispersing an identical aliquot of the inoculum into a suitable diluent, for example DPBST, using the same volume of diluent used to suspend the organism as listed above. Following inoculation in a validated neutralizing broth and incubation for an appropriate period of time, the inoculum control must be between $1.0\times10^5$–$1.0\times10^6$ cfu/mL The solutions were evaluated based on the performance requirement referred to as the "Stand-Alone Procedure for Disinfecting Products" (hereafter the "stand-alone test") and is based on the Disinfection Efficacy Testing for contact lens care products under the Draft Premarket Notification (510 (k)) Guidance Document For Contact Lens Care Products dated Apr. 1, 1996, prepared by the U.S. Food and Drug Administration, Division of Ophthalmic Devices. This performance requirement is comparable to current ISO standards for disinfection of contact lenses (revised 1995). The stand-alone test challenges a disinfecting product with a standard inoculum of a representative range of microorganisms and establishes the extent of viability loss at predetermined time intervals comparable with those during which the product may be used. There is a primary performance criteria and secondary performance criteria. The primary criteria for a given disinfection period (corresponding to a potential minimum recommended disinfection period) is that the number of bacteria recovered per mL must be reduced by a mean value of not less than 3.0 logs within the given disinfection period. The number of mold and yeast recovered per mL must be reduced by a mean value of not less than 1.0 log within the minimum recommended disinfection time with no increase at four times the minimum recommended disinfection time. If failing to pass this primary performance criteria, the secondary performance criteria exists which if passed qualifies the solution for the so-called "regimen test procedure" described in the FDA's Draft for Premarket Notification (510(k)) Guidance Document For Contact Lens Care Product, dated Apr. 1, 1996 or similarly described in the ISO/CEN regimen test procedure. Under the secondary performance criteria, there must be a combined log reduction for the mean values of all three bacteria of not less than 5.0 logs within the recommended given disinfection period. The minimum acceptable mean log reduction for any single bacterial type is 1.0 log. Stasis for the yeast and mold must be observed for the recommended disinfection period. If passing the secondary performance criteria (also referred to as minimum antimicrobial activity by the Stand-Alone Procedure), the regimen test challenges the proposed disinfection regimen (typically involving rubbing) with a standard inoculum of a representative range of microorganisms, in which test the inoculum is carried through the various stages of regimen by preliminary application to contact lenses.

The above testing procedures were used for evaluating the antimicrobial efficacy of disinfecting solutions such as prepared in Example 4, but which contain the bis(biguanide) alexidine at various concentrations extending from 1 ppm to 5 ppm for a testing period of one hour. The results are shown in Table 2 below.

TABLE 2

| Microorganism | Alexidine.2HCl Concentration (ppm) | Log Reduction (1 hr) |
|---|---|---|
| S. aureus | 1 | 1.6 |
| S. aureus | 2 | 4.3 |
| S. aureus | 3 | >4.8 |
| S. aureus | 4 | >4.8 |
| S. aureus | 5 | >4.8 |
| P. aeruginosa | 1 | >5.0 |
| P. aeruginosa | 2 | >5.0 |
| P. aeruginosa | 3 | >5.0 |
| P. aeruginosa | 4 | >5.0 |
| P. aeruginosa | 5 | >5.0 |
| S. marcescens | 1 | 3.5 |
| S. marcescens | 2 | >4.8 |
| S. marcescens | 3 | >4.8 |
| S. marcescens | 4 | >4.8 |
| S. marcescens | 5 | >4.8 |

The above results show that at 2.0 ppm the bis(biguanide) alexidine solution passes the one hour stand-alone test for bacteria, by which a 3 log reduction of all three bacteria is needed in the given disinfection time. According to the above results, at 1.0 ppm, alexidine will not pass the one hour stand-alone test for bacteria (failing with respect to *Serratia marcescens*). In order to pass the 1 hour stand-alone test, the fungi must also be tested, as in the next example.

EXAMPLE 6

This Example shows the antimicrobial efficacy of the solution of Example 4 according to the present invention using the testing procedures described in Example 5 above, but formulated at a concentration of 4.0 ppm alexidine and at time intervals of 15 min, 30 min, 45 min, and 60 min, which would represent 25%, 50%, 75% and 100% of a one hour minimum recommended disinfection time. The solution had been aged for 19 months at 25° C. The results are shown in Table 3 below.

TABLE 3

| Microorganism | Soak Period | Log Reduction |
|---|---|---|
| Staphylococcus aureus | 15 min | 2.5 |
| | 30 min | 4.4 |
| | 45 min | >4.9 |
| | 60 min | >4.9 |
| Pseudomonas aeruginosa | 15 min | 4.0 |
| | 30 min | >4.8 |
| | 45 min | >4.8 |
| | 60 min | >4.8 |
| Serratia marcescens | 15 min | 3.2 |
| | 30 min | >4.7 |
| | 45 min. | >4.7 |
| | 60 min | >4.7 |
| Candida albicans | 15 min | 1.9 |
| | 30 min | 2.5 |
| | 45 min | 2.7 |
| | 60 min | 2.8 |
| | 4 h | 3.4 |
| Fusarium solani | 15 min | 3.4 |
| | 30 min | 4.3 |
| | 45 min | 4.4 |
| | 60 min | 4.2 |
| | 4 h | >4.4 |

Based on the same criteria as described in Example 5, the alexidine solution formulated at 4.0 ppm is able to pass a stand-alone test (with no rub or rinse) at the 30 minute time point, 45 time point and the 60 minute time point. With respect to *Staphylococcus aureus* the 15 minute time point failed.

EXAMPLE 7

This Example shows the antimicrobial efficacy of a solution according to the present invention using the testing procedures described in Example 5 above. These tests were similar to Example 6 except with a different lot that had been aged for 18 months. The concentration of alexidine was formulated at 4.0 ppm and the time intervals were 15 min, 30 min, 45 min, and 60 min. The results are shown in Table 4 below.

TABLE 4

| Microorganism | Soak Period | Log Reduction |
| --- | --- | --- |
| Staphylococcus | 15 min | 3.7 |
| aureus | 30 min | 4.7 |
|  | 45 min | >4.8 |
|  | 60 min | >4.8 |
| Pseudomonas | 15 min | 4.2 |
| aeruginosa | 30 min | >4.8 |
|  | 45 min | >4.8 |
|  | 60 min | >4.8 |
| Serratia | 15 min | 3.0 |
| marcescens | 30 min | 4.7 |
|  | 45 min | >4.8 |
|  | 60 min | >4.8 |
| Candida | 15 min | 1.0 |
| albicans | 30 min | 1.7 |
|  | 45 min | 1.9 |
|  | 60 min | 2.1 |
|  | 4 hrs | 3.1 |
| Fusarium | 15 min | 2.4 |
| solani | 30 min | >4.5 |
|  | 45 min | >4.5 |
|  | 60 min | >4.5 |
|  | 4 hrs | >4.5 |

In the above testing, the alexidine passed the stand alone test at 30 minutes, 45 minutes, and 60 minutes, but only just passed the 15 minute stand-alone test with respect to *Serratia marcesens* and *Candida albicans*. It is clear that at 30 min, 45 min, and one hour stand-alone showed greater disinfection, easily passing the acceptance criteria.

EXAMPLE 8

This Example shows the antimicrobial efficacy of a solution according to the present invention using the testing procedures described in Example 5 above. For a final time, these tests were similar to Example 6 except with a different batch. The concentration of alexidine was formulated at 4.0 ppm and the time intervals were 15 mn, 30 min, 45 min, and 60 min, which would represent 25%, 50% and 100% of a one hour minimum recommended disinfection period. The solution had been aged 19 months at 25° C. The results are shown in Table 5 below.

TABLE 5

| Microorganism | Soak Period | Log Reduction |
| --- | --- | --- |
| Staphylococcus | 15 min | 3.5 |
| aureus | 30 min | >4.9 |
|  | 45 min | >4.9 |
|  | 60 min | >4.9 |
| Pseudomonas | 15 min | 3.3 |
| aeruginosa | 30 min | >4.8 |
|  | 45 min | >4.8 |
|  | 60 min | >4.8 |

TABLE 5-continued

| Microorganism | Soak Period | Log Reduction |
| --- | --- | --- |
| Serratia | 15 min | 2.5 |
| Marcescens | 30 min | 4.6 |
|  | 45 min | >4.7 |
|  | 60 min | >4.7 |
| Candida | 15 min | 0.9 |
| albicans | 30 min | 1.7 |
|  | 45 min | 1.8 |
|  | 60 min | 1.9 |
|  | 4 hrs | 2.6 |
| Fusarium | 15 min | 3.6 |
| solani | 30 min | >4.6 |
|  | 45 min | >4.6 |
|  | 60 min | >4.6 |
|  | 4 hrs | >4.6 |

In the above test, the alexidine solution passed the stand-alone test (without rubbing) at 30 minutes, 45 minutes, and 60 minutes, but did not pass the test at 15 minutes, since at 15 minutes the log reduction for *Serratia marcesens* was less than 3 logs and the number of the yeast *Candida albicans* was not reduced by at least 1 log. The results in Tables 3, 4, and 5 above show some variation due to the testing of different lots of the solutions described in Example 4 above, but that a 4.0 ppm alexidine solution would require at least about 30 minutes in order to pass a stand-alone procedure without rubbing.

COMPARATIVE EXAMPLE 9

This Example compares the antimicrobial efficacy of a solution according to the present invention in which alexidine is in an excipient of ReNu® MPS solution compared to an analogous solution containing PHMB in ReNu® MPS solution. Both solutions were borate buffered to enhance the efficacy of the biguanide and contained EDTA and Poloxamine surfactant similar to the solution of Example 4. ReNu is a registered tradmark of Bausch & Lomb of Rochester, N.Y.) The testing procedures used for evaluating the antimicrobial efficacy of disinfecting solutions was the same as in Example 5 above. The results are shown in Table 6 below.

TABLE 6

| Microorganism Tested | Time Tested | 1.0 ppm PHMB | 4.0 ppm Alexidine · 2HCl |
| --- | --- | --- | --- |
| Staphylococcus | 1 hr | 3.5 | >4.9 |
| aureus | 2 hr | 3.9 | >4.9 |
|  | 3 hr | >4.9 | >4.9 |
|  | 4 hr | >4.9 | >4.9 |
| Pseudomonas | 1 hr | 3.5 | >4.8 |
| aeruginosa | 2 hr | 4.0 | >4.8 |
|  | 3 hr | 4.1 | >4.8 |
|  | 4 hr | >4.8 | >4.8 |
| Serratia | 1 hr | 3.2 | 3.7 |
| marcescens | 2 hr | 4.2 | >4.7 |
|  | 3 hr | >4.7 | >4.7 |
|  | 4 hr | >4.7 | >4.7 |
| Candida | 1 hr | 2.9 | 2.9 |
| albicans | 2 hr | 3.0 | 4.3 |
|  | 3 hr | 3.4 | >4.7 |
|  | 4 hr | 3.4 | 3.9 |
|  | 24 hr | 4.3 | 4.6 |
| Fusarium | 1 hr | 0.4 | 3.1 |
| solani | 2 hr | 0.5 | 4.1 |
|  | 3 hr | 0.4 | 4.5 |
|  | 4 hr | 0.4 | 4.6 |
|  | 24 hr | 1.3 | >4.6 |

As indicated in Example 5, the acceptance criteria was that the number of bacteria recovered per mL must be reduced by a factor of not less than 99.9% (3 logs) with the minimum disinfection period (which would be recommended with the product, in label, package, and/or package insert instructions), and the number of mold and yeast recovered per mL shall be reduced by a factor of not less than 90% (1 log) within the minimum recommended disinfection time, with no increase at four times the minimum recommended disinfection time. The above results show that the 1.0 ppm PHMB did not pass the one hour stand-alone test, since the *Fusarium solani*, a mold, was not sufficiently reduced. In contrast, the 4.0 ppm alexidine solution according to the present invention passed the one hour stand-alone test, showing a reduction in the number of mold by 3.1 log after 1 hour. Presently, PHMB is used in an amount of about 1.0 ppm in commercial solutions for disinfecting soft lenses. It has been found that increasing the level of PHMB to 3.0 ppm results in clinical findings that suggest PHMB may be less safe than desirable, for use with soft contact lens. In contrast, as shown in the next example, based on rabbit studies, it has been found that a 4.0 ppm solution of alexidine would be very safe for human use in disinfecting soft lenses.

EXAMPLE 10

This example demonstrates the ocular toxicology of alexidine in solutions such as described in Example 4 above, but at various concentrations of the bis(biguanide). A series of formulations were prepared in which the amount of alexidine were, respectively 4 ppm (test 1), 6 ppm (test 2), 8 ppm (test 3), 10 ppm (test 4), 12 ppm (test 5), 15 ppm (test 6), 18 ppm (test 7), 22 ppm (test 8), 27 ppm (test 9), 33 ppm (test 10), 40 ppm (test 11) and 50 ppm (test 12). These test solutions of alexidine were used in soaking J&J Sure Vue® (etafilcon A) lenses (soft lenses) in 2.5 mL of solution for 1 week or more in order to reach maximal alexidine uptake.

An ocular irritation screening study was conducted in the rabbit to determine the threshold for ocular irritation. Eyes treated with the lenses were compared to a contralateral control eye. Treated lenses were placed on the right eye of rabbits; control lenses were placed on the left eye. Any lenses displaced from the eyes during the lens wear day were reinserted after rinsing with 0.9% sodium chloride USP solution (SC). Eyes were examined with the aid of a direct light source before lens placement, at 50–70 minutes, 7–8 hours, 23–24 hours, and 30–32 hours after placement. Macroscopic observations were recorded in accordance with criteria in the Draize[*] score system. The maximum total score is the sum of all scores obtained for the cornea, iris, and conjunctivae. Total maximum score possible is 110 per eye, 80 with respect to the cornea, 10 with respect to the iris, and 20 with respect to the conjunctivae.

[*]Draize, J. H., G. Woodward and H. O. Calvery. 1944. Methods for the study of irritation and toxicity of substances applied topically to the skin and mucous membranes. J. Pharmacol. Exp. Ther. 82:377–390.

The results of macroscopic ocular examinations for each animal appear in Table 7 below (weighted totals present).

TABLE 7

| | | | | POST LENS APPLICATION | | | | | | |
|---|---|---|---|---|---|---|---|---|---|---|
| Test No. | ppm Alexidine.2HCl | Prior to Lens Application | | 50–70 Minutes | | 7–8 Hours | | 23–24 Hours | | 30–32 Hours | |
| | | R | L | R | L | R | L | R | L | R | L |
| 1 | 4 | 0 | 0 | 2 | 2 | 2 | 0 | 2 | 0 | 2 | 2 |
| 2 | 4 | 0 | 0 | 2 | 2 | 2 | 2 | 2 | 2 | 2 | 2 |
| 3 | 4 | 0 | 0 | 2 | 2 | 2 | 2 | 2 | 2 | 2 | 2 |
| 4 | 6 | 2 | 0 | 2 | 2 | 2 | 0 | 2 | 0 | 2 | 0 |
| 5 | 6 | 2 | 2 | 2 | 2 | 2 | 2 | 2 | 2 | 2 | 2 |
| 6 | 6 | 2 | 2 | 2 | 2 | 2 | 0 | 2 | 0 | 2 | 0 |
| 7 | 8 | 0 | 0 | 2 | 0 | 2 | 0 | 2 | 2 | 2 | 2 |
| 8 | 8 | 2 | 2 | 2 | 2 | 2 | 2 | 2 | 0 | 2 | 2 |
| 9 | 8 | 2 | 2 | 2 | 2 | 2 | 2 | 2 | 2 | 2 | 2 |
| 10 | 10 | 2 | 0 | 2 | 0 | 4 | 0 | 2 | 0 | 2 | 0 |
| 11 | 10 | 2 | 2 | 2 | 0 | 2 | 0 | 2 | 2 | 2 | 2 |
| 12 | 10 | 0 | 0 | 2 | 0 | 4 | 2 | 0 | 0 | 0 | 0 |
| 13 | 12 | 2 | 0 | 2 | 2 | 2 | 2 | 2 | 2 | 2 | 2 |
| 14 | 12 | 2 | 2 | 2 | 2 | 2 | 2 | 2 | 2 | 2 | 2 |
| 15 | 12 | 2 | 2 | 2 | 2 | 2 | 2 | 2 | 2 | 2 | 2 |
| 16 | 15 | 0 | 0 | 2 | 2 | 4 | 0 | 2 | 0 | 2 | 0 |
| 17 | 15 | 2 | 2 | 4 | 2 | 4 | 0 | 2 | 2 | 2 | 2 |
| 18 | 15 | 0 | 0 | 2 | 0 | 4 | 0 | 0 | 0 | 2 | 0 |
| 19 | 18 | 2 | 0 | 2 | 2 | 6 | 2 | 2 | 0 | 2 | 0 |
| 20 | 18 | 2 | 2 | 2 | 2 | 6 | 2 | 2 | 2 | 2 | 2 |
| 21 | 18 | 2 | 2 | 2 | 2 | 6 | 2 | 2 | 2 | 2 | 2 |
| 22 | 22 | 2 | 0 | 2 | 2 | 11 | 0 | 2 | 0 | 2 | 2 |
| 23 | 22 | 2 | 2 | 2 | 2 | 11 | 0 | 2 | 0 | 2 | 2 |
| 24 | 22 | 0 | 0 | 2 | 0 | 11 | 0 | 2 | 0 | 2 | 0 |
| 25 | 27 | 2 | 0 | 2 | 2 | 13 | 2 | 2 | 2 | 2 | 0 |
| 26 | 27 | 2 | 0 | 2 | 2 | 11 | 2 | 2 | 2 | 2 | 0 |
| 27 | 27 | 2 | 2 | 2 | 2 | 6 | 2 | 2 | 2 | 2 | 0 |
| 28 | 27 | 2 | 0 | 2 | 2 | 11 | 2 | 7 | 2 | 7 | 2 |
| 29 | 27 | 2 | 0 | 2 | 2 | 11 | 2 | 7 | 2 | 7 | 2 |
| 30 | 27 | 2 | 0 | 2 | 2 | 9 | 0 | 2 | 0 | 2 | 0 |

R = Right (Test) Eye
L = Left (Control) Eye

When worn by rabbits, lenses soaked in 10 ppm Alexidine showed the first signs of increased ocular toxicity, with conjunctival reactions observed after 7–8 hours of lens wear. This sporadic conjunctival reaction was clearly defined at a dose of 15 ppm alexidine in solution and continued to become more severe as the dosage was elevated. Iridial involvement was observed at 22 ppm and corneal opacity was observed at 27 ppm. Conjuntival redness, chemosis, and discharge were the sole basis of the Draize findings for lens numbers until 22 ppm and 27 ppm (test nos. 8 and 9). Iritis, in addition to previously described findings were observed for lens number 8 and 9. The above results indicate that a formulation with 10 ppm of alexidine or more is not recommended for disinfecting soft contact lenses. The preferred formulation with 4 ppm alexidine, represents a 2.5-fold safety margin relative to the initial onset of any possible abnormal ocular health in rabbits.

EXAMPLE 11

This example illustrates shows the antimicrobial efficacy of solutions according to the present invention using the testing procedures described in Example 5 above, but specifically to determine the minimal concentration of alexidine to pass the secondary performance criteria, in order to meet the threshold requirements for a regimen involving rubbing of the lens with the solution. The concentrations of alexidine ranged from 1 ppm to 5 ppm and the time periods tested were 5 minutes and 10 minutes (The one-hour time period is shown in Example 6 above). The results are shown in Table 8 below.

TABLE 8

| Microorganism | Alexidine.2HCL Concentration (PPM) | Log Reduction at 5 Minutes | Log Reduction at 10 Minutes |
|---|---|---|---|
| S. aureus | 1.0 | 0.7 | 1.0 |
| S. aureus | 2.0 | 1.6 | 2.6 |
| S. aureus | 3.0 | 2.6 | 4.0 |
| S. aureus | 4.0 | 4.8 | 4.8 |
| S. aureus | 5.0 | 4.8 | >4.8 |
| P. aeruginosa | 1.0 | 0.5 | 3.2 |
| P. aeruginosa | 2.0 | 3.0 | 4.3 |
| P. aeruginosa | 3.0 | 3.8 | >5.0 |
| P. aeruginosa | 4.0 | 3.7 | >5.0 |
| P. aeruginosa | 5.0 | >5.0 | >5.0 |
| S. marcescens | 1.0 | 0.5 | 0.7 |
| S. marcescens | 2.0 | 0.8 | 1.8 |
| S. marcescens | 3.0 | 1.1 | 2.6 |
| S. marcescens | 4.0 | 2.0 | >4.8 |
| S. marcescens | 5.0 | 2.9 | >4.8 |

As indicated above, a one log reduction for each bacterial species with a total of a five log reduction for all three bacterial species is needed for passing entrance into the regimen test. The results show that for each bacterial species, a 2.0 ppm alexidine solution passes the 10 minute entrance into the regimen, but that a 1.0 ppm alexidine solution does not pass the 10 minute entrance into the regimen. (For the secondary performance criteria, only stasis would be required for the two fungal species.)

EXAMPLE 12

This example illustrates shows the antimicrobial efficacy of solutions according to the present invention using the testing procedures described in Example 5 above, but specifically to determine the minimal concentration of alexidine to pass the secondary performance criteria, in order to meet the threshold requirements for a regimen involving rubbing the lens with the solution. The concentration of alexidine in this set of tests was formulated at 4.0 ppm and the time periods tested were 2.5 minutes, 5 minutes, 7.5 minutes, and 10 minutes, which would represent a 25%, 50%, 75% and 100% testing of the a 10 minute minimum soaking period. The solution had been aged for 18 months. The results are shown in Table 9 below.

TABLE 9

| Microorganism | Soak Period (Minutes) | Log Reduction Exp. 1 | Log Reduction Exp. 2 | Log Reduction Exp. 3 |
|---|---|---|---|---|
| Staphylococcus aureus | 2.5 | 2.2 | 1.6 | 2.0 |
| | 5.0 | 2.7 | 2.0 | 2.8 |
| | 7.5 | 3.1 | 2.3 | 3.4 |
| | 10.0 | 3.5 | 2.7 | 3.9 |
| Pseudomonas aeruginosa | 2.5 | 2.4 | 1.9 | 2.7 |
| | 5.0 | 3.2 | 3.2 | 3.1 |
| | 7.5 | 3.4 | 3.8 | 4.1 |
| | 10.0 | >4.8 | >4.8 | 4.9 |
| Serratia marcescens | 2.5 | 0.5 | 0.8 | 0.8 |
| | 5.0 | 0.6 | 2.0 | 2.0 |
| | 7.5 | 0.9 | 2.8 | 2.2 |
| | 10.0 | 1.2 | 2.8 | 2.2 |
| Candida albicans | 2.5 | 0.0 | 0.1 | 0.0 |
| | 5.0 | 0.0 | 0.1 | 0.0 |
| | 7.5 | 0.6 | 0.5 | 0.4 |
| | 10.0 | 0.7 | 0.6 | 0.4 |
| | 40.0 | 2.1 | 1.0 | 1.0 |
| Fusarium solani | 2.5 | 2.5 | 2.5 | 2.2 |
| | 5.0 | 4.3 | 4.1 | 2.1 |
| | 7.5 | 4.6 | 4.4 | 2.4 |
| | 10.0 | >4.6 | 4.5 | 2.5 |
| | 40.0 | >4.6 | >4.5 | >4.6 |

The results show, although varying between tests (lots), the secondary performance criteria was met in all cases for a minimum soaking period of 10 minutes, and failed in all cases for a minimum soaking period of 2.5 minutes, with some variability in between these two time periods. The tests clearly show, however, that the solution satisfies the qualification test for regimen involving rubbing and a soak time of 10 minutes.

EXAMPLE 13

This example illustrates the preparation of aqueous disinfecting solutions used in the present method comprising a combination of alexidine and polyhexamtheylene biguanide (also referred to as PAPB or PHMB). The following components are used, in the indicated percent weight per total volume of solution:

| | Percent (w/v) |
|---|---|
| PAPB | 0.0008 |
| Alexidine.2HCL | 0.0002 |
| Poloxamine 1107** | 1.0 |
| Na$_2$EDTA | 0.11 |
| Boric Acid | 0.66 |
| Sodium Borate | 0.10 |
| Sodium Chloride | 0.54 |
| Distilled Water (qs) | 100.0 |

The solution is prepared by gradually heating 80 percent of the water to 80° C. while dissolving the disodium EDTA therein. The boric acid and sodium borate are added to the heated solution of disodium EDTA and dissolved. The sodium chloride is then added to the solution and dissolved, followed by the addition of surfactants. The solution is sterilized by autoclaving to 120° C. for 45 minute. After the solution is cooled to room temperature, the bis(biguanide) and PAPB are added through a sterile filter, followed by the balance of distilled water. The solution is packaged in sterilized plastic containers.

EXAMPLE 14

This Example illustrates the improved antimicrobial efficacy of a combination of alexidine with PAPB in an aqueous disinfecting solution for contact lenses. The testing procedures described in Example 5 above were followed to determine whether the primary performance criteria would be passed at time intervals of 5 min., 15 min, 30 min, and 4 hrs. The concentration of alexidine in this set of tests was formulated in amounts ranging from 0.0 to 4.0 ppm in combination with either 0.0 or 0.8 ppm alexidine, the latter the amount of PAPB currently used in commercial multi-purpose solutions for soft contact lenses. The results are shown in Table 10 below.

TABLE 10

| Alexidine.-2HCl (ppm) | PAPB (ppm) | Soak Period | Log Reduction S. marcescens | Log Reduction C. albicans |
|---|---|---|---|---|
| 0.5 | 0.8 | 5 min | — | 0.6 |
|  |  | 15 min | 2.0 | 1.1 |
|  |  | 30 min | 3.2 | 1.8 |
|  |  | 60 min | 4.3 | 3.5 |
| 1.0 | 0.8 | 5 min | — | 0.5 |
|  |  | 15 min | 2.6 | 1.1 |
|  |  | 30 min | 3.7 | 2.2 |
|  |  | 60 min | >4.3 | 4.2 |
| 2.6 | 0.8 | 5 min | — | 0.7 |
|  |  | 15 min | 2.7 | 2.2 |
|  |  | 30 min | >4.3 | 3.3 |
|  |  | 60 min | >4.3 | >4.2 |
| 4.0 | 0.8 | 5 min | — | 1.1 |
|  |  | 15 min | >4.3 | 3.0 |
|  |  | 30 min | >4.3 | >4.2 |
|  |  | 60 min | >4.3 | >4.2 |
| 0.5 | 0.0 | 5 min | — | 0.3 |
|  |  | 15 min | 0.6 | 1.0 |
|  |  | 30 min | 1.6 | −0.2 |
|  |  | 60 min | 2.5 | −0.1 |
| 2.6 | 0.0 | 5 min | — | 0.4 |
|  |  | 15 min | 2.2 | 0.5 |
|  |  | 30 min | >4.3 | 0.5 |
|  |  | 60 min | >4.3 | 1.4 |
| 0.0 | 0.8 | 15 min | — | 0.6 |
|  |  | 30 min | 1.3 | 0.8 |
|  |  | 45 min | 2.0 | 1.4 |
|  |  | 60 min | 3.1 | 2.9 |

The results show that the addition of alexidine to the polyhexametheylene biguanide very significantly improves antimicrobial efficacy, with the improved efficacy reaching a trade-off, for practical purposes, at about 4.0 ppm, such that any improved antimicrobial efficacy would be unlikely to be justified by the increased potential for toxicity at higher concentrations of the antimicrobial agents. With respect to *C. albicans*, there appears to be a synergistic effect at time periods of 15 minutes and 30 minutes, with the combination of 2.6 ppm alexidine and 0.8 ppm PAPB showing greater efficacy than the sum of 2.6 ppm alexidine by itself and 0.8 ppm PAPB by itself.

While the invention has been described in conduction with specific examples thereof, this is illustrative only. Accordingly, many alternatives, modifications, and variations will be apparent to those skilled in the art in light of the foregoing description and it is, therefore, intended to embrace all such alternatives, modifications, and variations as to fall within the spirit and scope of the appended claims.

We claim:

1. A method of cleaning and/or disinfecting a soft contact lens comprising:
   (a) rubbing the contact lens with an ophthalmically safe solution comprising the following components:
      (i) a microbiocidally effective amount of the hydrorhloride salt of a bis(biguanide) in the amount of about 2.0 to about 8.0 ppm, or a corresponding molar amount of the bis(biguanide) in the form of another water-soluble salt or the free base thereof, which bis(biguanide) has the following general formula:

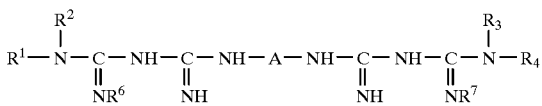

wherein $R^1$ and $R^4$ are independently selected from the group consisting of branched or unbranched alkyl having 4–12 carbon atoms, alkoxyalkyl ether or alkylsulfide thioether radical having 4–12 carbon atoms, or cycloalkyl or cycloalkyl-alkyl radical having 5–12 carbon atoms; $R^2$ and $R^3$ are independently selected from the group consisting of hydrogen, alkyl having 1–12 carbon atoms, alkoxyalkyl having 1–12 carbon atoms, or cycloalkyl or cycloalkyl-alkyl having 5–12 carbon atoms; $R^6$ and $R^7$ are independently selected from the group consisting of hydrogen and alkyl radical having 1–6 carbon atoms, and A in the above formula is a divalent group having 4–16 carbon atoms and is selected from the group consisting of alkylene, alkyloxyalkyl, and alkylsufide radical, wherein the aforesaid alkyoxyalkyl or alkylsulfide radicals are either a polymethylene chain interrupted with one or more oxygen and/or sulfur atoms or a polymethylene chain substituted with an alkoxy ($-OR^8$) or alkylthio ($-SR^9$) group, wherein $R^8$ and $R^9$ are independently selected from the group consisting of alkyl having 1–12 carbon atoms, or a cycloalkyl or cycloalkyl-alkyl having 5–12 carbon, or wherein A is a divalent polymethylelne group having 8 to 16 carbon atoms interrupted with a divalent radical of cyclohexane or diazacyclohexane;
      (ii) an effective amount of a buffering agent,
      (iii) an effective amount of a surfactant; and
   (b) soaking the rubbed contact lens from step (a) in the solution for a total period of time that is within a range of about 5 minutes to about 75 minutes; and
   (c) directly placing the treated lens on an eye of the wearer, such that a rinse with a different solution is not required.

2. The method of claim 1, wherein said total period of time for soaking is within a range of about 7.5 minutes to about 60 minutes.

3. The method of claim 1, wherein said total period of time for soaking is within a range of about 10 minutes to about 45 minutes.

4. The method of claim 1, wherein said total period of time for soaking is within a range of about 10 minutes to about 30 minutes.

5. The method of claim 1, wherein the surfactant is a neutral or non-ionic surfactant in the amount of 0.01 to 5.0 percent.

6. The method of claim 1, wherein the surfactant is a neutral or non-ionic surfactant having a plurality of poly(oxyalkylene) chains, each of the poly(oxyalkylene) comprises ($-OR$) repeat units, wherein R is independently an alkylene having 2 to 6 carbon atoms.

7. The method of claim 6, wherein the surfactant is a neutral or non-ionic surfactant which comprises a block copolymer of poly(ethyleneoxide) and poly(propylene oxide) segments.

8. The method of claim 1, wherein the said, amount is 2.5 to 6.0 ppm.

9. The method of claim 1 wherein said amount is 3:0 to 5.0 ppm.

10. The method of claim 1, wherein the bis(biguanide) has the following formula:

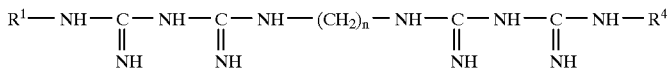

or water-soluble salts thereof, wherein $R^1$ and $R^4$ are independently selected from the group consisting of branched or unbranched alkyl, alkoxyalkyl ether or alkylsulfide thioether radical, and n is 5 to 7.

11. A method of cleaning and/or disinfecting a contact lens comprising:
(a) rubbing the contact lens with an ophthalmically safe solution comprising the following components:
  (i) microbiocidally effective amount of the hydrochloride salt of a bis(biguanide) in the amount of about 2.0 to about 8.0 ppm, or a corresponding molar amount of the bis(biguanide) in the form of another water-soluble salt or the free base thereof, which bis(biguanide) has the following general formula:

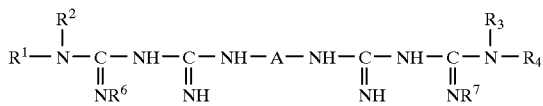

wherein wherein $R^1$ and $R^4$ are independently selected from the group consisting of branched or unbranched alkyl having 4–12 carbon atoms, alkoxyalkyl or alkylsulfide radical having 4–12 carbon atoms, or cycloalkyl or cycloalkyl-alkyl radical having 5–12 carbon atoms; $R^2$ and $R^3$ are independently selected from the group consisting of hydrogen, alkyl having 1–12 carbon atoms, alkoxyalkyl having 1–12 carbon atoms, or cycloalkyl or cycloalkyl-alkyl having 5–12 carbon atoms; $R^6$ and $R^7$ are independently selected from the group consisting of hydrogen and alkyl radical having 1–6 carbon atoms, and A in the above formula is a divalent group having 4–16 carbon atoms and is selected from the group consisting of an alkylene, alkyloxyalkyl, and alkylsufide radical, wherein the aforesaid alkyoxyalkyl or alkylsulfide radicals are either a polymethylene chain interrupted with one or more oxygen and/or sulfur atoms or a polymethylene chain substituted with an alkoxy (—$OR^8$) or alkylthio (—$SR^9$) group, wherein $R^8$ and $R^9$ are independently selected from the group consisting of alkyl having 1–12 carbon atoms, or a cycloalkyl or cycloalkyl-alkyl having 5–12 carbon, or wherein A is a divalent polymethylene group having 8 to 16 carbon atoms interrupted with a divalent radical of cyclohexane or diazacyclohexane;
  (ii) one or more polymeric biguanides in the total amount of about 0.1 to about 3.0 ppm, which polymeric biguanides have the following formula:

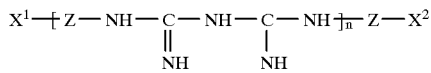

wherein Z is an organic divalent bridging group which may be the same or different throughout the polymer, n is at least 3, and $X^1$ and $X^2$ are independently selected from the groups —$NH_2$ and

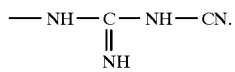

(iii) an effective amount of a buffering agent;
  (iv) an effective amount of a surfactant present; and
(b) soaking the rubbed contact lens from step (a) in the solution for a total period of time that is within a range of about 5 minutes to about 75 minutes; and
(c) directly placing the treated lens on an eye of the wearer, such that a rinse with a different solution is not required.

12. The method of claim 11, wherein said total period of time for soaking is within a range of about 7.5 minutes to about 60 minutes.

13. The method of claim 11, wherein said total period of time for soaking is within a range of about 10 minutes to about 30 minutes.

14. The method of claim 11, wherein the solution has a pH between 6.0 and 8.0 and further comprises an tonicity agent and a buffering agent.

15. The method of claim 11, wherein the solution comprises a surfactant that is a neutral or non-ionic surfactant.

16. The method of claim 11, wherein the surfactant is a neutral or non-ionic surfactant having a plurality of poly(oxyalkylene) chains, each of the poly(oxyalkylene) comprises (—OR) repeat units, wherein R is independently an alkylene having 2 to 6 carbon atoms.

17. The method of claim 11, wherein said amount of the bis(biguanide) is about 2.5 to about 6.0 ppm.

18. The method of claim 11, wherein said amount of the bis(biguanide) is about 3.0 to about 5.0 ppm.

19. The method of claim 1 or 2, wherein the bis(biguanide) has the following formula:

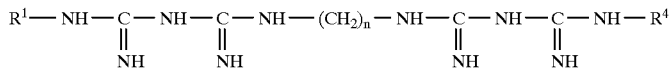

or water-soluble salts thereof, wherein $R^1$ and $R^4$ are independently selected from the group consisting of branched or unbranched alkyl, alkoxyalkyl ether or alkylsulfide thioether radical, and n is 5 to 7.

20. The method of claim 11, wherein the polymeric biguanides are a mixture of polymers having the following formula:

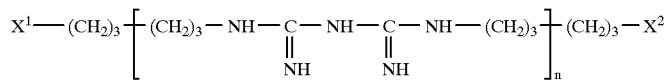
wherein $X^1$ and $X^2$ are as defined above.
* * * * *

UNITED STATES PATENT AND TRADEMARK OFFICE
CERTIFICATE OF CORRECTION

PATENT NO. : 5,965,088
DATED : Oct. 12, 1999
INVENTOR(S) : Andrea M. Lever, O. William Lever, Jr.

It is certified that error appears in the above-identified patent and that said Letters Patent is hereby corrected as shown below:

In Column 25, line 63, "hydrorhloride" should read -- hydrochloride -- .

In Column 26, line 62, "said, amount is" should read -- said amount of said bis(biguanide) is -- .

In Column 26, line 64, "said amount is 3:0" should read -- said amount of said bis(biguanide) is 3.0 -- .

Signed and Sealed this

Fifth Day of September, 2000

Attest:

Q. TODD DICKINSON

Attesting Officer

Director of Patents and Trademarks